(12) United States Patent
Ahlmen

(10) Patent No.: US 7,077,134 B2
(45) Date of Patent: Jul. 18, 2006

(54) ANESTHETIC REFLECTOR

(75) Inventor: Christer Ahlmen, Sollentuna (SE)

(73) Assignee: Maquet Critical Care AB, Solna (SE)

( * ) Notice: Subject to any disclaimer, the term of this patent is extended or adjusted under 35 U.S.C. 154(b) by 88 days.

(21) Appl. No.: 10/760,822

(22) Filed: Jan. 20, 2004

(65) Prior Publication Data
US 2004/0149281 A1    Aug. 5, 2004

(30) Foreign Application Priority Data
Jan. 23, 2003    (SE)    .................... 0300161

(51) Int. Cl.
A62B 7/10    (2006.01)

(52) U.S. Cl. ............ 128/205.12; 128/203.12; 128/204.18

(58) Field of Classification Search .......... 128/203.12, 128/204.18, 203.13, 204.21, 205.12
See application file for complete search history.

(56) References Cited

U.S. PATENT DOCUMENTS

| | | | |
|---|---|---|---|
| 5,044,361 A | | 9/1991 | Werner et al. |
| 5,237,990 A | * | 8/1993 | Psaros et al. ......... 128/204.21 |
| 5,471,979 A | | 12/1995 | Psaros et al. |
| 5,505,768 A | | 4/1996 | Altadonna |
| 5,678,537 A | * | 10/1997 | Bathe et al. ........... 128/203.12 |
| 5,694,924 A | * | 12/1997 | Cewers ................. 128/204.21 |
| 6,116,235 A | | 9/2000 | Walters et al. |
| 6,206,002 B1 | * | 3/2001 | Lambert ................ 128/205.12 |

FOREIGN PATENT DOCUMENTS

| | | |
|---|---|---|
| DE | OS 36 33 724 | 4/1988 |
| WO | WO 97/14465 | 4/1997 |
| WO | WO 02/26306 | 4/2002 |

* cited by examiner

*Primary Examiner*—Mital Patel
(74) *Attorney, Agent, or Firm*—Schiff Hardin LLP

(57) ABSTRACT

An anesthetic reflector has a housing internally containing two externally accessible gas channels and a filter of a material for releasable sorption of gas-borne anesthetic agent. The filter is movable between the gas channels to expose the same portion of the filter to the interior of each channel in turn.

6 Claims, 4 Drawing Sheets

ANESTHETIC REFLECTOR

BACKGROUND OF THE INVENTION

1. Field of the Invention

The present invention relates to an anesthetic reflector of the type allowing re-use of exhaled anesthetic agents in inhalation anesthesia.

2. Description of the Prior Art

Anesthetic reflectors for the re-use of gas-borne anesthetic agents are well known and are described in, for example, U.S. Pat. Nos. 5,044,361 and 5,471,979. These reflectors generally have a housing in which there is provided openings that delimit a common gas flow channel through the interior of the housing. Retained within the housing and disposed internally the gas flow channel is a filter for the alternating sorption and desorption of anesthetic agent from and into gas passing along the common flow channel. In use, these anesthetic reflectors are located within pneumatic circuits of anesthetic ventilator systems so that anesthetic-rich expiration gas, which is exhaled by a patient into the pneumatic circuit during an expiration phase of a patient breathing cycle, passes along the common flow channel and through the filter in one flow direction and so that inspiration gas in the pneumatic circuit, which is to be supplied to the patient during a subsequent inspiration phase of the patient breathing cycle, passes along the common flow channel, usually but not necessarily in the opposite flow direction, and through the filter. The filter acts to retain anesthetic agent borne by the expiration gas and then to release this retained anesthetic agent into the inspiration gas for re-supply (reflection) to the patient.

One problem with these known reflectors is that the common flow channel constitutes a "dead-space" in which carbon dioxide ($CO_2$), that is also exhaled by the patient, remains after an expiration phase, and therefore may be undesirably re-supplied to the patient with the inspiration gas.

In order to overcome this problem it is known to provide an additional filter for retaining $CO_2$ in inspiration gas passing from the anesthetic gas reflector. Such a $CO_2$ filter may be integral with the reflector or may be a separate unit.

A further problem with the known reflectors is that in order to be able to quickly reduce the anesthetic concentration in the inspiration gas that otherwise would pass through the reflector, an additional gas flow line and associated flow controller are required by which the anesthetic sorption filter may be selectively by-passed. It is further known to realize this by-pass line as a separate flow channel within the housing of the reflector.

SUMMARY OF THE INVENTION

It is an object of the present invention to provide an anesthetic reflector, and an inhalation anesthesia system employing such an anesthetic reflector, wherein the above-discussed problems associated with known anesthesia reflectors are at least alleviated.

This object is achieved in accordance with the principles of the present invention in an anesthetic reflector having a housing with two externally accessible gas channels formed therein, and containing a filter for releasable sorption of gas-borne anesthetic agent, wherein the filter is movable between the gas channels to expose the same portion of the filter to the interior of each channel, in alternation.

The above object also is achieved in an inhalation anesthesia system employing such an anesthetic reflector.

By arranging for the filter to be movable, either by rotation or translation, between the two gas flow channels in turn, then at least the problem of the re-supply of the dead-space $CO_2$ may be alleviated.

Moreover, the inventive anesthetic reflector has the further advantage that by selectively halting the movement of the filter during the provision of inhalation anesthesia, the concentration of anesthetic in the inspiration gas for delivery to a patient may be relatively quickly reduced without the need for a separate by-pass conduit.

DESCRIPTION OF THE PREFERRED EMBODIMENTS

Figure 1:
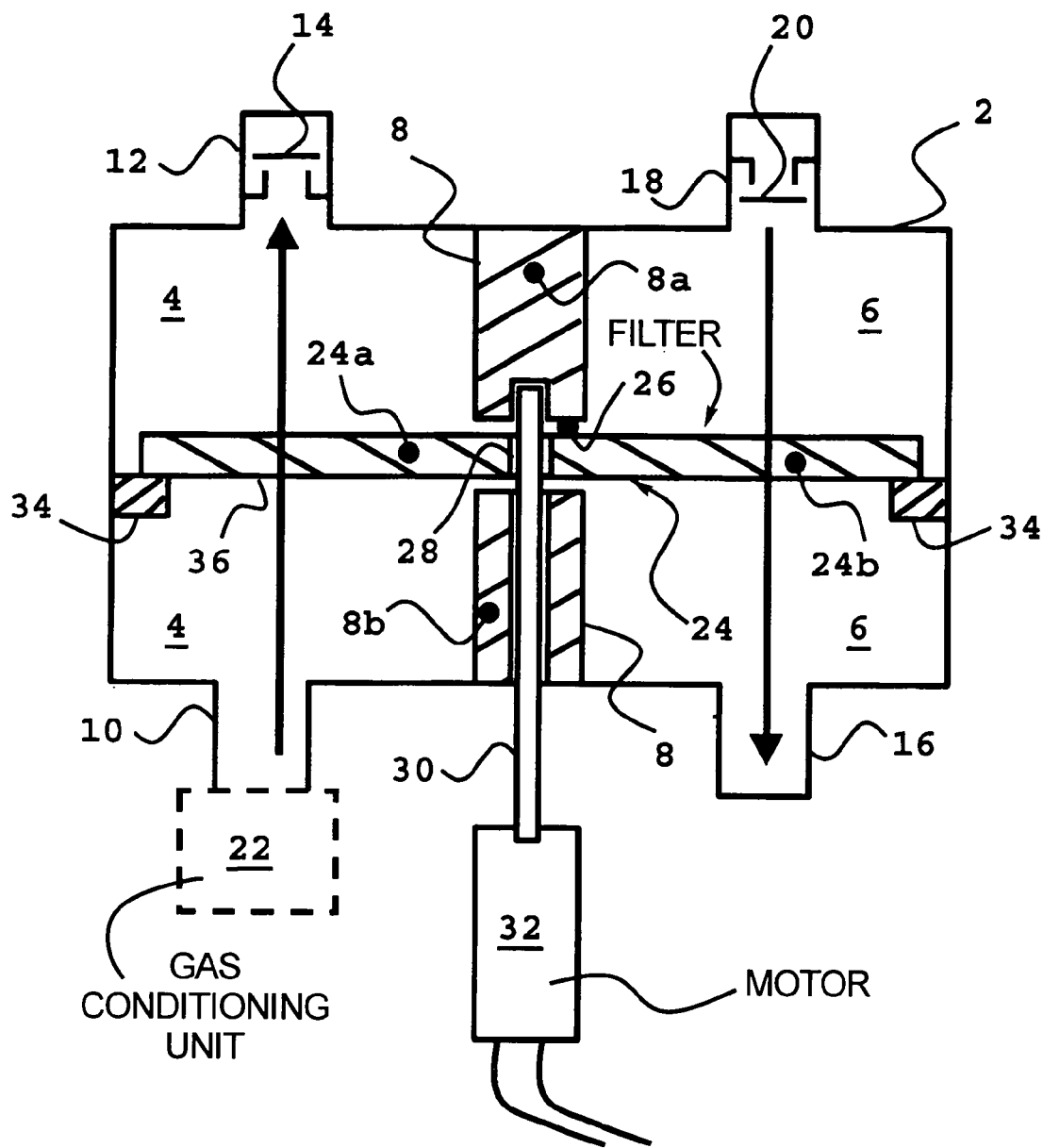
FIG. 1 shows a first embodiment of an anesthetic reflector according to the invention.

The anesthetic reflector illustrated in FIG. 1, has a housing 2, that in the present example is of a cylindrical form, containing a first gas channel 4 and a second gas channel 6, here separated by a common wall portion 8. Two gas ports 10,12 are provided in the housing 2 to connect the first gas channel 4 externally of the housing 2 in a flow-through configuration. One of the two gas ports 10,12 (in this embodiment the port 12) is provided with a one-way valve 14 so that flow-through within the first gas chamber 4 is in one direction only. Similarly, two gas ports 16,18 are provided in the housing 2 to connect the second gas channel 6 externally of the housing 2, also in a flow-through configuration. One of the two gas ports 16,18 (in this embodiment the port 18) is provided with a one-way valve 20 so that flow-through is in one direction only. The two one-way valves 14,20 are mutually orientated such that flow through is in opposite directions in the gas channels 4,6. In this manner the first gas channel 4, for example, can be connected to an inspiration gas line of a pneumatic circuit of an inhalation anesthesia system (not shown) and the second gas channel 6 can then be connected to an expiration line of the pneumatic circuit.

The present embodiment of the anesthetic reflector may be connected to a gas conditioning unit 22 (shown with broken lines) that is provided in the inspiration line preferably immediately upstream of the gas port 10, by which inspiration gas will enter the first gas channel 4. The unit 22 is configured to at least warm the incoming inspiration gas. In this manner the desorption of sorbed anesthetic gas will be enhanced. Indeed thermal energy may be supplied to enhance desorption in a number of ways apparent to those skilled in the art. The unit 22 also may be adapted to humidify the incoming inspiration gas.

A disc-shaped filter 24 has a suitable anesthetic sorption material, for example activated carbon cloth or granules, and is preferably removably retained within the housing 2 and arranged to pass through an opening 26 (shown exaggerated for clarity) in the common wall portion 8, which may be formed of two separate sections 8a, 8b. In the present embodiment a section 24a of the sorbing material of the filter 24 extends into and essentially divides the first gas channel 4 and a section 24b extends into and essentially divides the second gas channel 6. The filter 24 is provided with a through-hole 28 for removable engagement with a rotatable shaft 30 by which the filter 24 can be rotated. In the present embodiment a motor 32 is connectable to the shaft 30 and is operable to rotate it.

A projection 34 also may be provided around the inner surface of each gas channel 4,6 against which a peripheral portion of a surface 36 of the filter 24 can seal. In this manner the amount of gas in each of the gas channels 4,6 that passes through the filter 24 may be increased and so the reflection properties of the reflector enhanced.

Figure 2A:
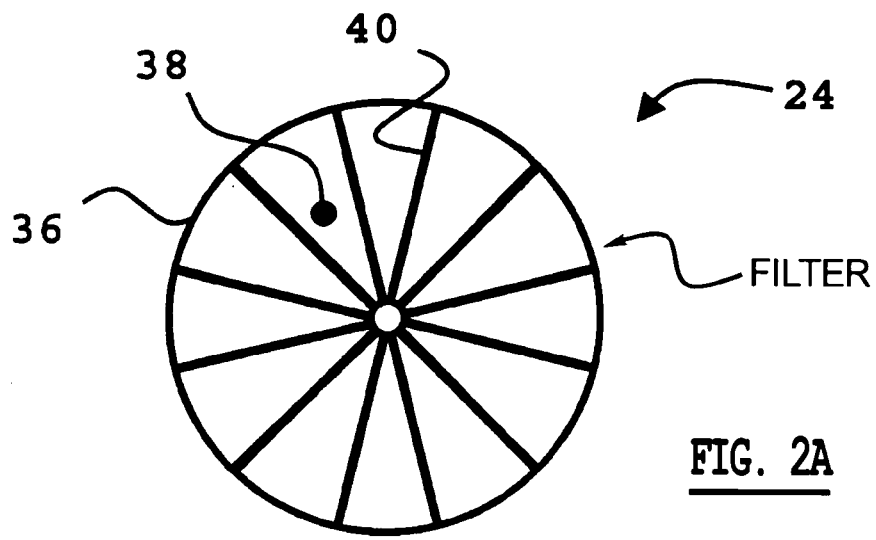
FIG. 2A shows a filter usable in the reflector of FIG. 1.
Figure 2B:
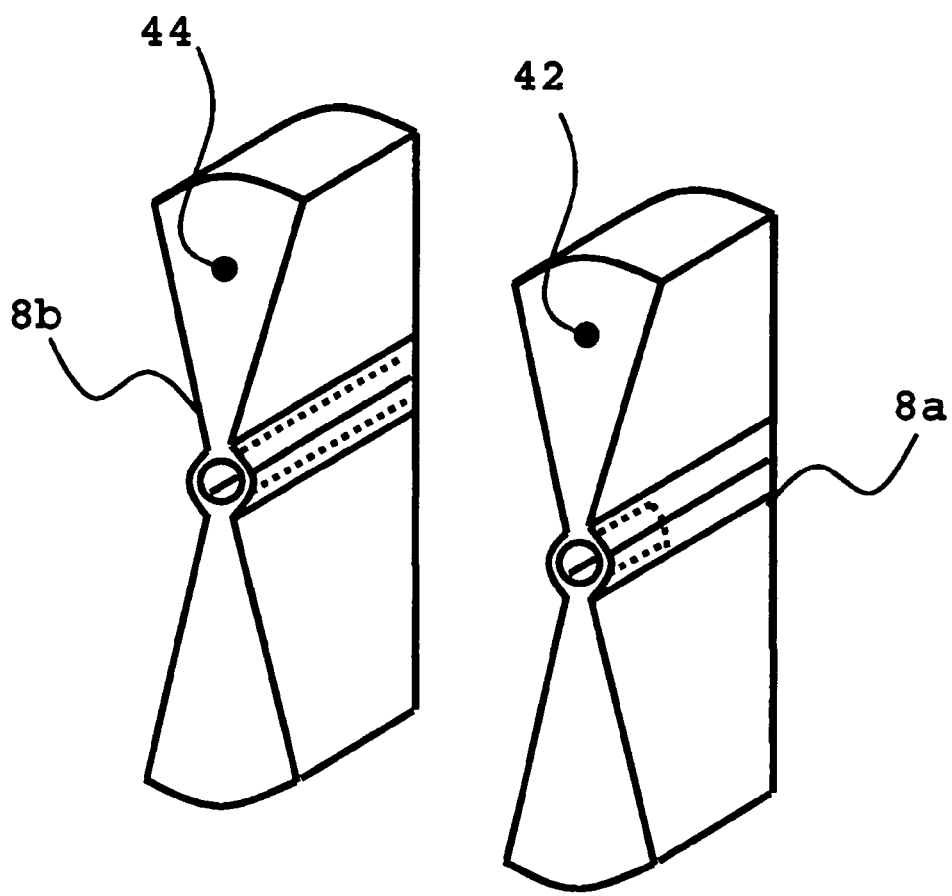
FIG. 2B shows an example of the common wall portion of the reflector of FIG. 1 usable with the filter of FIG. 2.

A suitable configuration of the filter 24 is illustrated in FIG. 2A with cooperating sections 8a, 8b of the common wall portion 8 illustrated in FIG. 2B. The sorbing material of the filter 24 is divided into a number of identical segments, indicated generally at 38, using dividing members that are in the present example shown as compressible ribs (indicated generally at 40). These ribs 40 protrude from each of the opposing surfaces, for example the surface 36, of the filter 24 and in use form a gas-tight seal against a cooperating facing surface, 44 say, of the common wall portion 8. To further minimize leakage of gas between the two gas channels 4,6 the surfaces of the common wall section 8 that face opposite surfaces of the filter 24 are shaped to conform to the shape of the segments 38. An example of this is illustrated in FIG. 2B. Cooperating sections 8a, 8b that constitute the common wall section 8 are each provided with a surface 42,44 respectively that in use faces an opposing surface, 36 for example, of the filter 24. Each surface 42,44 of the sections 81,8b is formed to conform substantially to the shape of an opposing pair of segments 38 of the filter 24. It is intended that in use the ribs 40 that delimit this opposing pair of segments 38 contact and are compressed against a corresponding surface 42,44 to inhibit transport of gas between the channels 4,6.

Figure 3:
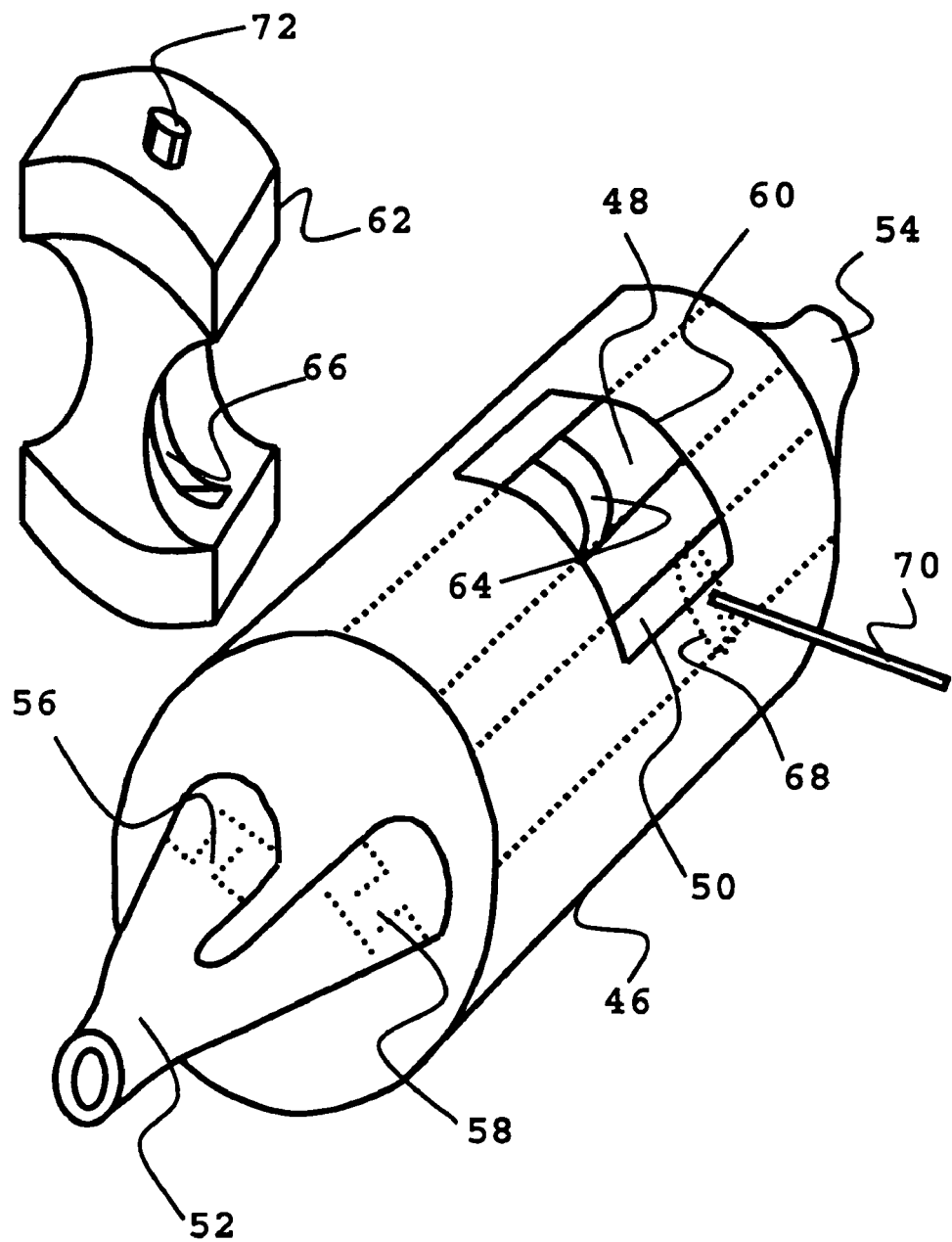
FIG. 3 shows a second embodiment of an anesthetic reflector according to the invention.

A further embodiment of the anesthetic reflector according to the present invention is illustrated in FIG. 3. A housing 46 has an internal arrangement of a first gas channel 48 and a second gas channel 50 that are externally accessible by means of a pair of gas ports 52,54 that arranged at opposite ends of the housing 46 to provide a common flow path for the first 48 and the second 50 gas channels. It will be appreciated that these gas ports 52,54 may be fixedly or removably attached to the housing 46. A one-way valve 56,58 is associated with respectively the first 48 and the second 50 gas channel and cooperate to permit gas flow in an opposite direction in each channel 48,50. In the present example these valves 56,58 are both located in a respective branch of one 52 or preferably both 52,54 (only one 52 shown) gas ports but may of course be located in their respective gas channel 48,50 internal the housing 46.

An opening 60 is provided in the housing 46 into which a filter holder 62 is removably received. A slot 64 is formed in each of the channels 48,50 (only one shown) in an opposing arrangement and located beneath the opening 60. A corresponding slot 66 is provided through the body of the filter holder 62 which cooperates with the slots 64 in each of the channels 48,50 to form a conduit through which an anesthetic sorption filter 68 can slide in a reciprocating movement between internal each of the channels 48,50 in turn. A rod 70 is also provided to releasably attach to the filter 68 when the filter 68 is located within the housing 46 and is sized to be externally accessible when the filter 68 is in either channel 48,50. In the present example, the rod 70 is devised for a push fit connection to the filter 68. For this purpose, a releasable detent 72 is integrated in the filter holder 62 and may be actuated to move in to and out of contact with a peripheral portion of the filter 68 when located within the slot 66 to hold the filter 68 within the filter holder 62 as the rod 70 is attached or detached.

Figure 4:
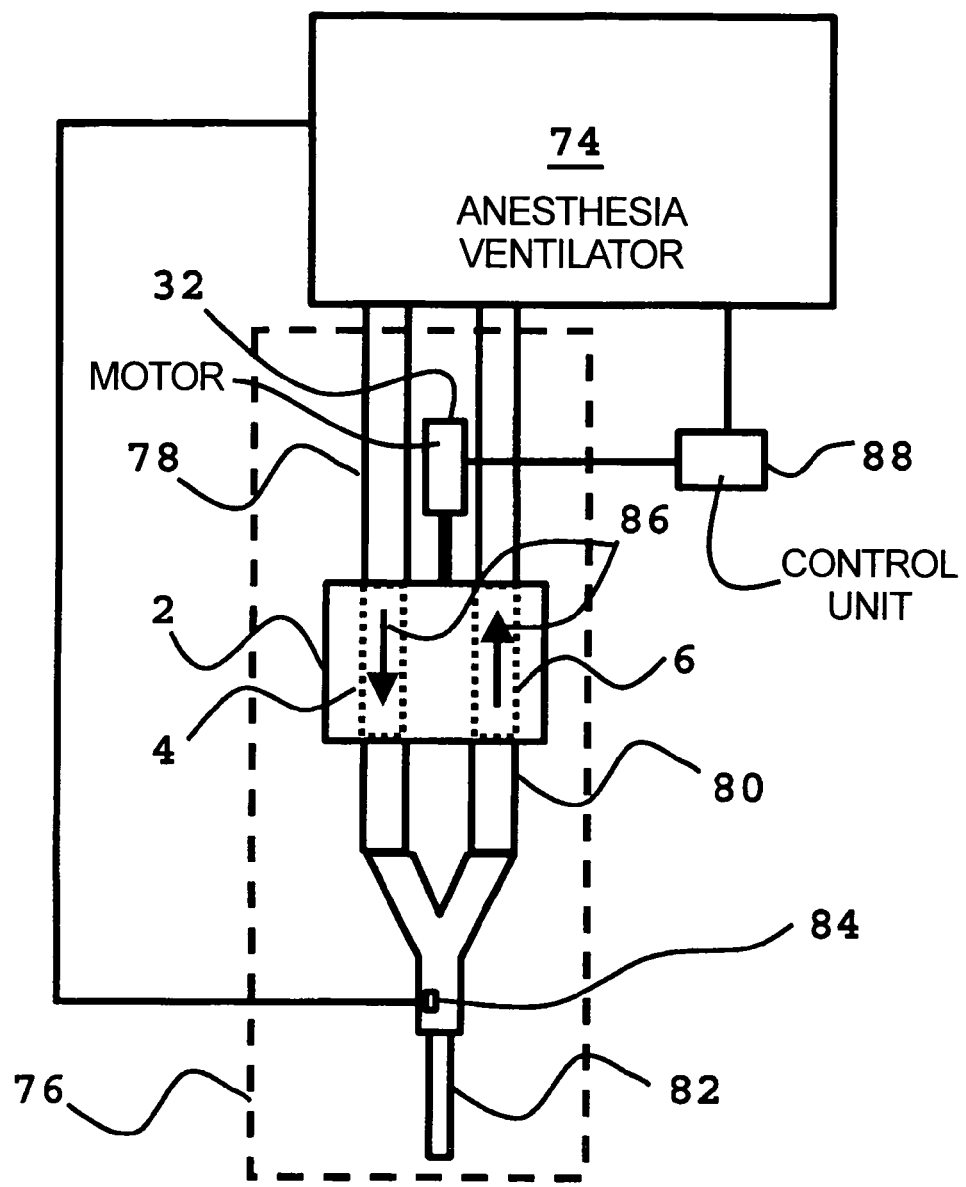
FIG. 4 shows an inhalation anesthesia system incorporating an anesthetic reflector according to the present invention.

An inhalation anesthesia system is shown in FIG. 4 and has a known anesthesia ventilator 74 for the metering and controlled delivery of an anesthetic containing breathing gas and a conventional pneumatic circuit 76 for guiding the flow of gases between the ventilator 74 and the airways of a patient (not shown). The pneumatic circuit 76 in the present example has an inspiration line 78, through which gas will flow towards the patient, an expiration line 80, through which gas will flow from the patient and a patient line 82, providing a common gas flowpath to and from the patient and in gas connection to both the inspiration line 78 and the expiration line 80. An anesthetic concentration sensor 84 may be placed in the patient line to sense the concentration of anesthetic in both the inspiration and the expiration gas and to provide a measure of the same as a control parameter to the ventilator 74. An anesthetic reflector according to the present invention such as is, for example, described above with respect to FIG. 1 is also provided as a part of the system. The housing 2 of the reflector is connected in line with the inspiration line 78 and with the expiration line 80 and is orientated such that the one-way valves 14,20 (not shown in FIG. 4) permit gas flow within the inspiration line 78 through only the first gas channel 4 and gas flow within the expiration line 80 through only the second gas channel 6, as indicated, in the present example, by the arrows 86 that are visible on an outer surface of the housing 2 for user orientation purposes.

It will be apparent to those skilled in the art that when a reflector according to the present invention, such as is for example described above in respect to FIG. 3, is employed having only one pair of gas ports 52,54 then the reflector housing 46 may be connected in-line to the common gas flow path that is provided by the patient line 82 of the anesthesia system.

The motor 32 is coupled to rotate the disc shaped filter 24 of FIG. 1 and is operably connected to a control unit 88 which controls the motor 32 in order to achieve a desired rotation of the filter 24 between the two gas channels 4,6. The desired rotation is preferably selected in order to avoid saturation of the filter 24 with exhaled anesthetic and to minimize $CO_2$ re-breathing and is dependent on one or more parameters that is typically either controlled or monitored by the ventilator 74, such as the frequency of breathing, the minute volume and the concentration of anesthetic. The control unit 88 is therefore operably connected to the ventilator 74 to receive an indication of the one or more parameters.

For example, assuming that the gas-holding volume of the disc shaped filter 24 is 80 ml then 40 ml will lie in the expiration side 6 and contains therefore about 5 vol % $CO_2$ (that is about 2 ml $CO_2$). If an acceptable level of re-breathing is 0.4 ml, which would be the case for even for small tidal volumes (a tidal volume of 200 ml would then have 0.2 vol % of $CO_2$), then a suitable rotational speed would be one tenth of a revolution per breath since this would mean that one fifth of the amount of expired $CO_2$ will appear in the inspiration side 4.

It will be appreciated by those skilled in the art that the control unit 88 may control the motor 32 to provide an intermittent rotation of the disc 24 or provide an oscillation of the disc 24 provided that the portion, for example 24b, of the filter 24 that, during an exhalation phase of a patient breathing cycle, was located within the second channel 6 to retain anesthetic present in the exhalation gas is moved to be located within the first channel 4 to release the retained anesthetic into the inspiration gas flowing through the first channel 4 during an inspiration phase of a patient breathing cycle.

Additionally, the control unit 88 may be configured to halt the rotation of the disc filter 24 for one or more breathing cycles, for example in response to a manually input signal. This permits a relatively rapid reduction in the amount of anesthetic released from the filter 24 into the inspiration gas flowing in the inspiration line 78. Additionally or alternatively a bias flow of anesthetic free gas through the gas channel 6 connected to the expiration line 80 may be provided during an expiration phase to flush anesthetic from the portion 24*b* of the filter 24 in that channel 6.

Although modifications and changes may be suggested by those skilled in the art, it is the intention of the inventor to embody within the patent warranted hereon all changes and modifications as reasonably and properly come within the scope of his contribution to the art.

I claim as my invention:

1. An anesthetic reflector comprising:
    a housing having two externally accessible, separated gas channels proceeding through the housing;
    a filter disposed in said housing for releasable sorption of gas-borne anesthetic agent; and
    said filter being mounted in said housing so as to be movable between said gas channels to expose the same portion of said filter to an interior of each of said channels, in alternation.

2. An anesthetic reflector as claimed in claim 1 wherein said filter is mounted in said housing for reciprocating movement between said two gas channels.

3. An anesthetic reflector as claimed in claim 1 wherein said filter is mounted in said housing for rotational movement through said two gas channels.

4. An anesthetic reflector as claimed in claim 3 wherein said two gas channels are disposed in said housing substantially parallel to each other and cooperate with said filter to simultaneously expose different portions of said filter to the interior of each channel.

5. An anesthetic reflector as claimed in claim 4 wherein said filter is divided into a plurality of segments separated by dividing members protruding from a surface of said filter, and said housing having a common wall section separating said two gas channels with a wall section surface facing said surface of said filter, said dividing members cooperating with said surface of said wall section to inhibit transport of gas between said two channels.

6. An inhalation anesthesia system comprising:
    an anesthetic ventilator;
    a pneumatic circuit connected to said anesthetic ventilator and adapted for communication with airways of a patient for conducting gas in opposite flow directions between said anesthetic ventilator and the air waves; and
    an anesthetic reflector having a housing connected in said pneumatic circuit, said housing having two separated gas channels proceeding through the housing, respectively for gas flow in said opposite directions, and a filter disposed in said housing for releasable sorption of gas-borne anesthetic agent, the filter being mounted in the housing for movement between said gas channels to expose the same portion of said filter to an interior of each of said channels, in alternation, with gas in said pneumatic circuit flowing in only one direction through the respective channels of the anesthetic reflector.

\* \* \* \* \*